United States Patent [19]
Klein

[11] Patent Number: 4,457,714
[45] Date of Patent: Jul. 3, 1984

[54] DENTAL BRIDGE AND METHOD OF DENTAL BRIDGE FABRICATION

[76] Inventor: Warren Z. Klein, 1137 E. 5th St., Brooklyn, N.Y. 11230

[21] Appl. No.: 359,519

[22] Filed: Mar. 18, 1982

[51] Int. Cl.³ .............................................. A61C 13/22
[52] U.S. Cl. ..................................... 433/180; 433/213
[58] Field of Search .............. 433/173, 178, 171, 177, 433/180, 182, 218, 219, 225

[56] References Cited

U.S. PATENT DOCUMENTS

| 446,769 | 2/1891 | Clowes | 433/180 |
| 1,738,460 | 2/1929 | Stark | 433/180 |

FOREIGN PATENT DOCUMENTS

| 420023 | 11/1934 | United Kingdom | 433/183 |

*Primary Examiner*—Robert Peshock
*Attorney, Agent, or Firm*—Gottlieb, Rackman & Reisman

[57] ABSTRACT

An integrally formed prefabricated dental bridge which allows complete fitting and attachment during one visit to a dentist. The bridge includes a vertically-oriented pontic element, and a pair of horizontally-extending bars disposed in line with each other on opposite sides of the pontic element. The biting surfaces of the two teeth adjacent the missing tooth have grooves formed in them for seating respective ones of the two horizontally-extending bars. The pontic element is then shaped by grinding to have the appearance of a natural looking tooth, and the two bars are covered by filling material applied to the grooves of the adjacent teeth.

14 Claims, 6 Drawing Figures

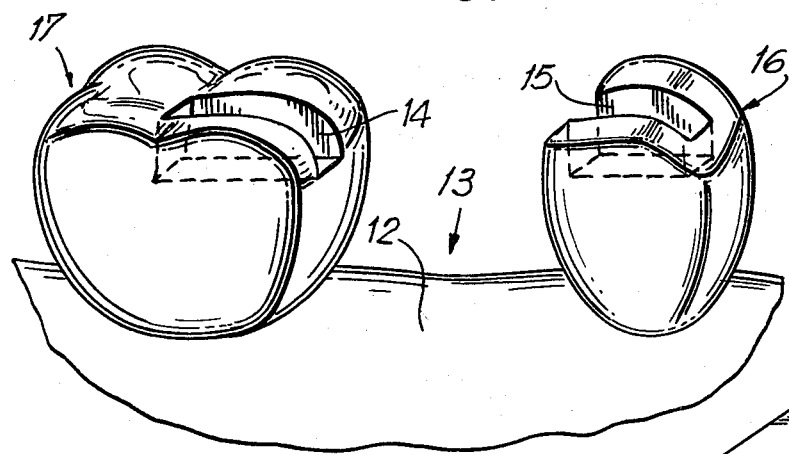
FIG. 1
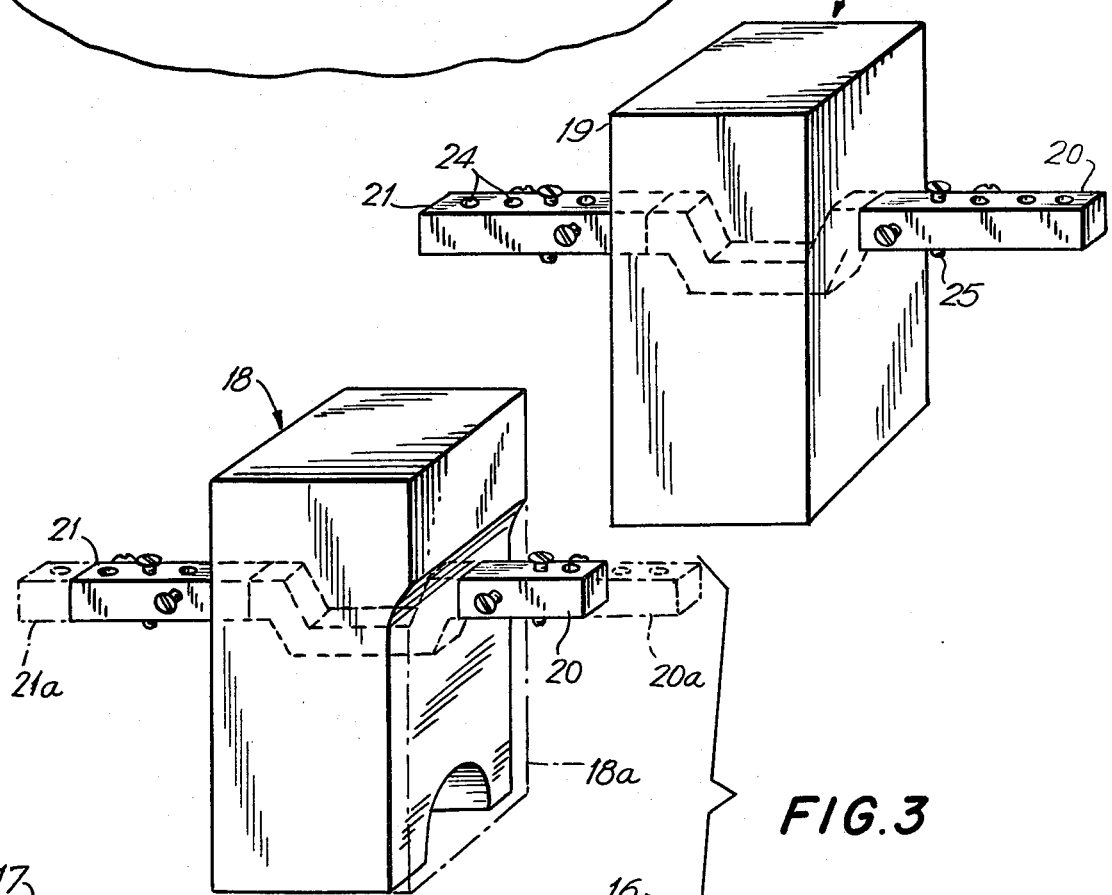
FIG. 2
FIG. 3
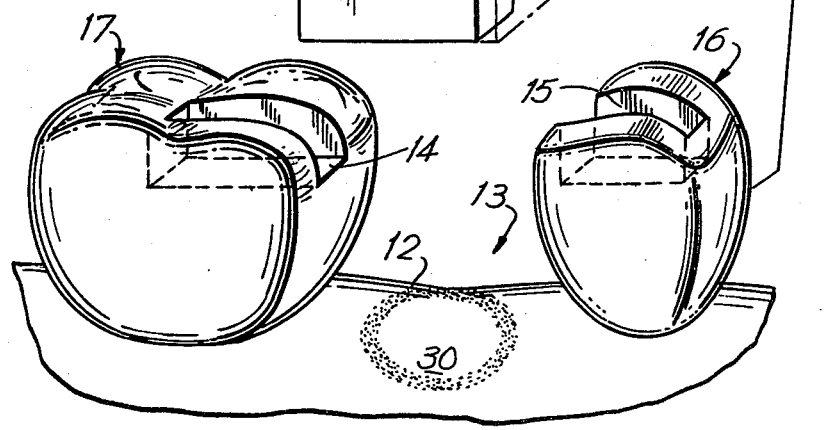

DENTAL BRIDGE AND METHOD OF DENTAL BRIDGE FABRICATION

DESCRIPTION

This invention relates to dental bridges, and more particularly to a dental bridge which allows start-to-finish fabrication and attachment during one sitting.

It is well known that dental bridgework is an involved process, which includes the taking of impressions, the fabrication of castings, and the processing of acrylic or the baking of porcelain. Temporary crowns or bridges must usually be made, and several visits to a dentist are required. The overall process is expensive, requires considerable skill on the part of a laboratory technician, and is carried out at two different sites—in the dentist's office and the technician's laboratory—and at different times. While the standard technique requires gross cutting down of tooth, there are other methods of bridge formation, e.g., etching with an acid in order to form a bond, which require less tooth preparation. But even these methods require the taking of impressions, the making of models and the employ of outside technicians.

Still another problem with conventional bridgework is that if a tooth is extracted, a long waiting period is necessary before it is replaced. Healing must take place while the space which previously contained the extracted tooth is left open. Alternatively, an adjacent tooth must be cut down so that a temporary bridge may be attached, thus adding to the trauma. But perhaps the greatest problem with conventional approaches is that they are all expensive, almost prohibitively so to a major portion of the population.

It is a general object of my invention to provide a dental bridge and method for shaping and attaching it that overcome the aforesaid problems.

The practice of my invention does not require any impressions, models, castings, acrylic processing or baking of procelain. Nor does it require the employ of laboratory technicians. There is minimal destruction of tooth structure and the entire process can be carried out in about one hour, at one sitting. The bridge is prefabricated so that the entire job can be done on the first visit to a dentist's office. Although the invention is described below in terms of the use of permanent filling material, the use of temporary filling material immediately after an extraction allows the fabrication of a temporary bridge; following healing, the bridge can be processed to its final form and then permanently secured in place. Relatively little skill is required on the part of the dentist in tooth preparation. The same prefabricated bridge may be used in many different positions, on either the right or left side of the mouth, and on either the upper or lower jaw. The bridge can be used with tilted teeth without concern being given to parallelism. In different forms, the prefabricated bridge can also be used to replace multiple missing teeth, and it can also be used to stabilize a mobile tooth whose prognosis is questionable while replacing an adjacent missing tooth.

Briefly, in accordance with the principles of my invention and in the illustrative embodiment thereof, I provide a single-piece prefabricated bridge having two connected part so that the bridge is an integral structure. The central part of the bridge—the pontic—is a rectangularly-shaped element, larger than the tooth to be replaced, and is made of a material which is compatible with dental tissues, is abrasion-resistant, and is sufficiently strong to withstand biting forces. Conventional dental-grade acrylic and porcelain materials may be used for the "tooth" element. Extending out of the two sides of the tooth element are two rigid bars, preferably made of conventional dental-grade chrome-cobalt or silver-palladium alloy for the two respective pontic materials. Grooves are drilled in the two teeth which are adjacent to the extracted tooth which is to be replaced. The tooth element of the bridge is shaped by grinding its material away so that, with the two bars seated in the grooves of the adjacent teeth, the tooth element has the appearance of an ordinary tooth conforming to the general pattern of teeth in the patient's mouth. Optional screws and screw holes on the bars may be used if they are necessary to properly position the bridge within the grooves of the adjacent teeth; in this way, repeated shaping of the tooth element while the device is removed from the patient's mouth allows the device to be seated subsequently in the identical position time after time. Following shaping of the tooth element and satisfactory seating of the bridge in the patient's mouth, conventional quartz-filled composite filling material is used to cover the side bars and to fill up the grooves in the adjacent teeth.

It is important to note that relatively little preparation of the adjacent teeth is required. A single groove in the biting surface of each of the adjacent teeth is all that is necessary. No impressions are required, nor need models be made. Even prior art methods which utilized acid-etching bonding techniques, and which required the removal of less tooth structure, still required the need for taking impressions and making models.

It is to be appreciated that bar formations have been used in the prior art to stabilize teeth and to splint them together. Although not standard practice, it appears that such bars could be used to form bridges; a bar could be fitted between the two teeth which are adjacent to an empty space, an impression could be taken, and a laboratory technician could then fabricate an artificial tooth and secure it to the bar in accordance with the previously taken impression. But even this technique is disadvantageous in that multiple sessions with the dentist are required, not to mention the employ of a laboratory technician.

Another prior art technique goes back as far as 1891; U.S. Pat. Nos. 446,769 and 3,641,670 are exemplary of patents which disclose this technique. A bar or other rigid member is applied in the mouth and secured to the two teeth which are adjacent to the empty space to be filled. The bar is not provided with a prefabricated central element which can be shaped to the desired appearance of an artificial tooth. Instead, material is applied in the mouth to the bar, and adapted to fit the gums and the bite. Such methods have the disadvantage of requiring the use of porous materials because the materials have to be able to harden at mouth temperature. Such porous materials harbor bacteria, and because they are placed directly against the gums they give rise to chronic gum irritation.

Another prior art method is exemplified by U.S. Pat. No. 1,211,494. The technique disclosed in this patent also involves the drilling of grooves in two adjacent teeth. However, the technique requires the fitting of two separate materials together, and further requires soldering outside of the mouth.

Other prior art methods, which are similar in some aspects to the method of my invention, are exemplified by U.S. Pat. Nos. 1,369,509; 1,376,645; 1,688,621; 2,213,964 and 2,573,804. However, all of the techniques disclosed in these patents require combining two or more materials either by setting in the mouth, or by soldering or by baking outside of the mouth. As such, all prior art methods require tedious and time-consuming work, the need for multiple visits to a dentist, considerable technical skill and expense, or the use of materials which must be added or combined in the mouth.

An important feature of my invention is the provision of a prefabricated, single-piece bridge. The only major work required on the part of the dentist is the shaping of the tooth element itself. (In some cases, the side bars may have to be shortened by cutting away their ends, but this is a trivial step.) But even the shaping of the tooth element is a relatively simple task. There is no need to add materials or parts together in order to adapt the bridge to the adjacent teeth, the gums, or the opposing teeth. The bridge can be secured to the adjacent teeth with the filling materials currently in use and, because the bridge is prefabricated outside the mouth, it can be made of materials which are the most bio-compatible.

Further objects, features and advantages of my invention will become apparent upon consideration of the following detailed description in conjunction with the drawing, in which:

FIG. 1 depicts the first step in the method of my invention, namely, the drilling of grooves in the biting surfaces of the two teeth which are adjacent to the space to be filled;

FIG. 2 depicts the prefabricated dental bridge of my invention;

FIGS 3-5 depict the subsequent steps in my method; and

Figure 4:
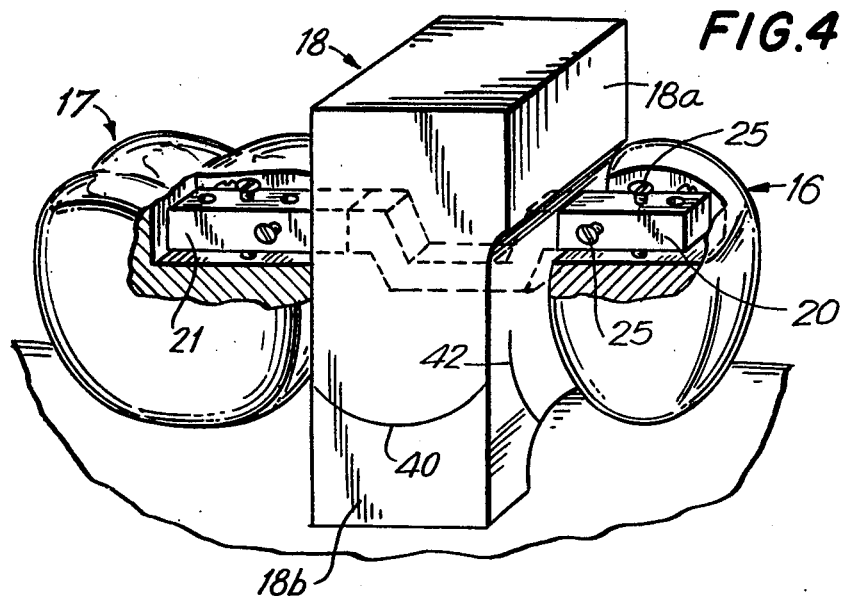

FIG. 1 depicts gum 12, with lower molar 17 and lower first bicuspid 16. The numeral 13 represents the empty space which is to be filled, an artificial tooth to be substituted for the missing second bicuspid. In the first step of the procedure, cavity preparations 14, 15 are drilled in the biting surfaces of respective teeth 17, 16. The cavity preparations, or grooves, can be formed even if there are existing fillings or crowns. Each groove must be wide enough to accommodate one of the side bars on the prefabricated dental bridge.

The dental bridge itself is shown in FIG. 2. The bridge 18 includes a vertically-oriented central section 19 which is rectangularly shaped and preferably made of acrylic or porcelain. A single horizontally-extending metal bar (which need not be regular in shape) extends through the central section so that the prefabricated bridge is an integral device having an artificial tooth section and two, preferably in-line, side bars 20, 21. It is not necessary that the two side bars be connected internally of the tooth element, although this is preferred. If a continuous metal bar is used, it is preferred that it have an irregular, non-linear shape inside the tooth element, as shown, in order to securely fix the two pieces to each other.

The prefabricated dental bridge of my invention comes in different sizes. What will usually be done is to select a bridge for use whose tooth element has front-to-back and vertical dimensions larger than those of the tooth to be replaced—to permit shaving away of material and proper shaping of the pontic. As will become apparent below, the sides of the tooth element will usually have to be ground away so that the element can properly fit between the two remaining teeth. In order for a proper fit to be achieved, it is necessary that the initial width of the central element not be too much smaller than the gap between the teeth; otherwise, the space between the two teeth 16, 17 will not be completely filled. In general, the tooth element has a configuration different from that of a natural looking tooth; its horizontal dimensions are larger than those of the tooth to be replaced, as is its vertical dimension. This is not to say, however, that the pontic has to be rectangularly shaped. It might have an elliptical cross-section, for example, to reduce the amount of material shaving which would otherwise be required. Also, the pontic may be shaped like a tooth, but oversized relative to the natural tooth to be replaced.

Because the sides of the tooth element can be ground away, it is not necessary to provide a dental bridge for every possible gap which may have to be filled. A single bridge size suffices for a range of gaps; the larger the gap, the greater the amount of material which must be ground away. It is also contemplated that a set of bridges may be provided in different colors, so that the dentist can select the appropriate color for the particular patient.

It is also to be understood that while the illustrative embodiment of the invention depicts only a single central section, for forming only a single tooth, a bridge may be provided with one central section large enough to replace two teeth. In the case of a bridge where a large central section for two teeth is provided, the bars would extend longer on each side in order to be able to held by as many as two teeth on each side for greater support.

FIG. 2 also depicts several screw holes 24 on each side bar, and several locating screws 25. Use of the screws is optional, but preferred. It will be appreciated that when the side bars are ultimately fitted in grooves 14, 15 (after the bottom of the tooth element is ground away as will be described), there may not necessarily be a tight fit. This is especially true if in forming the grooves 14, 15 too much tooth material is removed. In such a case, the bridge would not be firmly seated. While this is not a problem insofar as final securement is concerned inasmuch as the bridge is secured in place with filling material, it does make the subsequent shaping more difficult. It is required of the dentist that he grind material away from the tooth element so that a tooth of the desired shape be formed. This is accomplished by placing the bridge in the patient's mouth, marking the tooth element where processing is required, performing the processing, and then placing the bridge back in the patient's mouth to check the results. The shaping becomes much more difficult if each time that the bridge is reinserted in the patient's mouth it assumes another position.

For this reason, it is highly desirable to provide a mechanism for tightly fitting the bars in the grooves of the adjacent teeth so that a repeatable fit is obtained each time that the bridge is put in place. Toward this end, the screw holes and screws are provided. Screws which are inserted in horizontal screw holes effectively increase the width of the bar at the screw locations. One or more screws, in the same or opposite directions, may be placed in the two bars. As for the height of the bridge relative to the adjacent teeth, this can be controlled by longer vertical screws, these screws passing all the way through the bars if they are used. In such a case, it is the bottom of a screw which supports the bridge in an adjacent tooth as the processing proceeds. (In the final step, of course, filling material is applied and the hardened filling material supports the bridge along with the screws. The unused holes in the bars get filled with the filling material and thus serve to aid in securing the bridge in place.)

FIG. 3 depicts the manner in which the bridge is initially placed in the prepared teeth. In the event either or both of the bars are too long and cannot fit within their respective grooves, the ends of the bars, depicted by the numerals 20a and 21a, are shortened by grinding them away with an abrasive. Opposing sides 18a of the central tooth element are then shaved down with an abrasive disc, to the extent necessary, until the width of the tooth element is small enough such that it can be inserted vertically between teeth 16, 17. Due to the vertical length of the central section, it will not be possible at first to fully insert the tooth element and have the two bars seated in the grooves—even if screws 25 are used. Thus the bottom of the central secton must also be shaved down with an abrasive disc. Toward this end, dye material 30 may be applied to gum 12; as the central section is forced down, the dye material registers at the bottom—thus informing the dentist which regions must be further shaved down. The procedure is repeated until the sides of the cental section are sufficiently shaved down so that the unit can be inserted between the adjacent teeth, the bottom of the central section is sufficiently shaved down so that it matches the shape of the gum, and the bars are sufficiently shortened so that they can be seated in the grooves.

As mentioned above, screws 25 can be used in the side bars in order to achieve a repeatable firm fit. FIG. 4 illustrates the bridge in place after the bottom and sides have been processed. It is to be appreciated that the amount of shaving down required at the bottom of the central section can be minimized by employing vertical screws, thereby raising the entire device. Of course, the bars must remain fully contained within the side grooves and enough space must be left to cover them with filling material. Also, to whatever extent shaving down of the bottom of the central section is avoided at this stage, it must be compensated for later on by additional shaving down of the upper surface as will be described shortly.

It will be seen from FIg. 4 that the bottom of the central section extends down past the gum line on the sides. To avoid such an unsightly appearance, a horizontal marking 40 is made on both the front and back 18b of the central section, in line with the bottom of the adjacent teeth. Thereafter, with the bridge removed from the patient's mouth, the central section is shortened and rounded at the bottom so that the resulting tooth will appear to be equal in length to the length of the adjacent teeth. Comparable vertical lines 42 are drawn on each side 18a, in both the cheek and tongue regions, so that the front-to-back dimension of the tooth being processed can be made equal to the comparable dimensions of the adjacent teeth, using the same shaping procedure. Markings are also made on top of the pontic to indicate required shaving.

Figure 5:
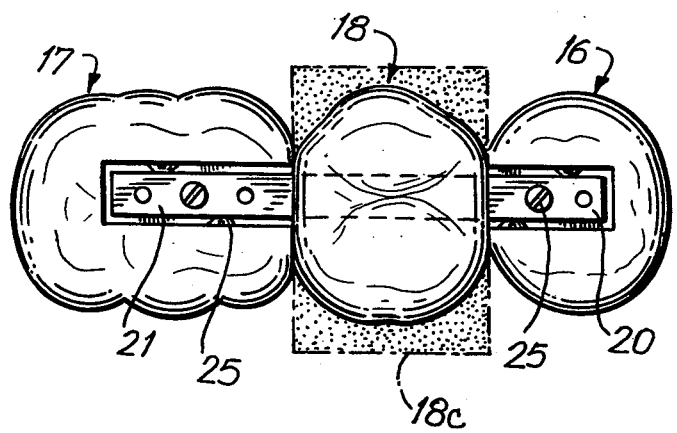

FIG. 5 is a top view which illustrates seating of the bridge in the adjacent teeth. The region 18c represents material of the tooth element which is removed in accordance with the markings made on the top of the pontic.

In the next step, the top of the tooth is shaped for a proper bite. Conventional marking paper may be used to register the bite, with the necessary regions of the upper surface of the tooth element being shaved down so that the bite is corrected.

After the completely shaped tooth is polished, the grooves in the adjacent teeth are filled with conventional filling material (temporary material if it is contemplated that additional shaping will be required later on, e.g., such as immediate placement after extraction and final shaping after healing). Following hardening of the filling material, the excess may be trimmed away.

Prior to the final filling step, if the central section is made of acrylic material, it may be stained with any quick-setting acrylic stain material now in use for better color matching if desired. If the central section is made of porcelain, individualized staining may be applied as is now done, with subsequent glazing in a furnace if desired. Alternatively, polishing alone without glazing will be sufficient in most cases.

Figure 6:
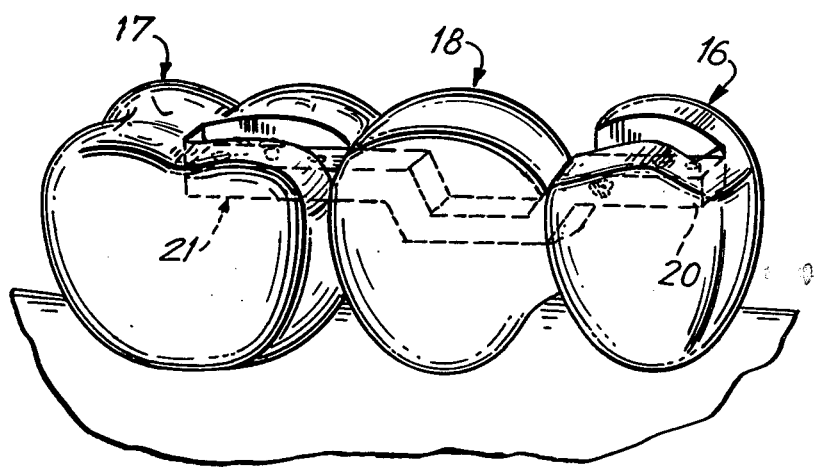
FIG. 6 illustrates the finished bridge in place.

FIG. 6 is a perspective view of the finished bridge, in place in the patient's mouth.

If the pontic is made of acrylic material, its top region may be fabricated of standard quartz-filled composite, the combination being baked onto the bar during manufacture. The advantage of such a combination is that the acrylic material touches the gum and can be polished to avoid gum irritation. The composite material is more abrasion-resistant and better for the bite. Use of procelain material for the pontic makes the shaping more difficult, but the finished bridge is stronger and maintains its color better.

To match the natural tooth and pontic colors, and in particular the vertical changes in shading, the pontic may be fabricated in horizontal layers of different color shades. Shaping of the sides of the pontic will thus not affect the color. It is also contemplated that pontics be provided in kit form, each kit including a multiplicity of pontics have different sizes and colors.

Although the invention has been described with reference to a particular embodiment it is to be understood that this embodiment is merely illustrative of the application of the principles of the invention. Numerous modifications may be made therein and other arrangements may be devised without departing from the spirit and scope of the invention.

I claim:

1. A starting product for the production of an integrally formed prefabricated dental bridge comprising an oversized vertically-oriented central pontic element, and a pair of horizontally-extending bars disposed on opposite sides of said central pontic element, said central pontic element being made of material which can be ground away and having a configuration larger than that of the natural tooth to be replaced.

2. An integrally formed prefabricated dental bridge in accordance with claim 1 wherein at least one of the horizontal dimensions of said central pontic element is larger than that of a natural tooth which is to be replaced by the dental bridge.

3. An integrally formed prefabricated dental bridge in accordance with claim 2 wherein the vertical dimension of said central pontic element is larger than that of a natural tooth which is to be replaced by the dental bridge.

4. An integrally formed prefabricated dental bridge in accordance with claim 3 wherein said pair of horizontaly-extending bars are comprised of a single bar which passes through said central pontic element.

5. An integrally formed prefabricated dental bridge in accordance with claim 4 wherein said single bar has a non-linear shape within said central pontic element.

6. An integrally formed prefabricated dental bridge in accordance with claim 5 wherein said horizontally-extending bars include adjustable locating means thereon.

7. An integrally ormed prefabricated dental bridge in accordance with claim 1 wherein said pair of horizontally-extending bars are comprised of a single bar which passes through said central pontic element.

8. An integrally formed prefabricated dental bridge in accordance with claim 7 wherein said single bar has a non-linear shape within said central pontic element.

9. An integrally formed prefabricated dental bridge in accordance with claim 8 wherein said horizontally-extending bars include adjustable locating means thereon.

10. An integrally formed prefabricated dental bridge in accordance with claim 1 wherein said horizontally-extending bars include adjustable locating means thereon.

11. An integrally formed prefabricated dental bridge in accordance with claim 1 wherein said pontic element is made of acrylic material with a biting region made of quartz-filled composite material.

12. A method of making a said starting product being dental bridge from an integrally formed prefabricated device; said device having an oversized vertically-oriented central pontic element and a pair of bars disposed on opposite sides of said central pontic element, said central pontic element being made of material which can be ground away and having a configuration larger than that of the natural tooth to be replaced; comprising the steps of:
(a) forming a groove on the biting surface of each of the two teeth which are adjacent to a missing tooth,
(b) seating the pair of horizontally-extending bars of said device in respective ones of said grooves,
(c) shaping said central pontic element to have the appearance of a natural looking tooth, and
(d) filling said grooves and covering the horizontally-extending bars therein with filling material.

13. A method in accordance with claim 12 wherein the horizontal and vertical dimensions of said central pontic element are larger than the corresponding dimensions of a natural tooth which is to be replaced, and in step (c) said central pontic element is shaped by grinding away the material thereof.

14. A method in accordance with claim 13 wherein said horizontally-extending bars include adjustable locating means thereon, and in step (b) said locating means are adjusted such that said horizontally-extending bars seat tightly in the respective grooves.

* * * * *